US00PP18629P2

(12) United States Plant Patent
Klemm

(10) Patent No.: US PP18,629 P2
(45) Date of Patent: Mar. 18, 2008

(54) ***GERANIUM* PLANT NAMED 'KLEPZ05148'**

(50) Latin Name: *Pelargonium×hortorum*
Varietal Denomination: KLEPZ05148

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/527,871

(22) Filed: Sep. 27, 2006

(51) Int. Cl.
*A01H 5/00* (2006.01)

(52) U.S. Cl. ..... Plt./325
(58) Field of Classification Search ..... Plt./325
See application file for complete search history.

(56) References Cited

U.S. PATENT DOCUMENTS

PP13,202 P2 * 11/2002 Klemm ..... Plt./326

OTHER PUBLICATIONS

UPOV ROM GTITM Computer Database, GTI Jouve Retrieval Software 2007/02 Citations for 'KLEPZ05148'.*

* cited by examiner

*Primary Examiner*—Wendy Haas
(74) *Attorney, Agent, or Firm*—C. A. Whealy

(57) ABSTRACT

A new and distinct cultivar of Zonal *Geranium* plant named 'KLEPZ05148', characterized by its upright and rounded plant habit; freely branching habit; large bright green-colored leaves; freely flowering habit; semi-double pale yellow-colored flowers; and good garden performance.

1 Drawing Sheet

Botanical designation: *Pelargonium×hortorum.*
Cultivar denomination: 'KLEPZ05148'.

BACKGROUND OF THE INVENTION

The present invention relates to a new and distinct cultivar of Zonal *Geranium*, botanically known as *Pelargonium×hortorum,* and hereinafter referred to by the name 'KLEPZ05148'.

The new Zonal *Geranium* is a product of a planned breeding program conducted by the Inventor in Stuttgart, Germany. The objective of the breeding program is to create new freely-branching and uniform Zonal *Geranium* cultivars with early flowering habit and attractive foliage and flower coloration.

The new Zonal *Geranium* originated from a cross-pollination made by the Inventor in Stuttgart, Germany in 1996 of a proprietary selection of *Pelargonium×hortorum* identified as code number Z W 001, not patented, as the female, or seed, parent with a proprietary selection of *Pelargonium×hortorum* identified as code number Z BS 001, not patented, as the male, or pollen, parent. The cultivar KLEPZ05148 was discovered and selected by the Inventors as a single flowering plant from within the progeny of the stated cross-pollination in a controlled environment in Stuttgart, Germany in 1997.

Asexual reproduction of the new Zonal *Geranium* by vegetative terminal cuttings in a controlled environment in Stuttgart, Germany since 1998, has shown that the unique features of this new Zonal *Geranium* are stable and reproduced true to type in successive generations.

SUMMARY OF THE INVENTION

The cultivar KLEPZ05148 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEPZ05148'. These characteristics in combination distinguish 'KLEPZ05148' as a new and distinct cultivar of Zonal *Geranium*:

1. Upright and rounded plant habit.
2. Freely branching habit.
3. Large bright green-colored leaves.
4. Freely flowering habit.
5. Semi-double pale yellow-colored flowers.
6. Good garden performance.

Plants of the new Zonal *Geranium* differ primarily from plants of the female parent selection in the following characteristics:

1. Plants of the new *Geranium* have larger leaves than plants of the female parent selection.
2. Plants of the new *Geranium* have large flowers than plants of the female parent selection.

Plants of the new Zonal *Geranium* differ primarily from plants of the male parent selection in the following characteristics:

1. Plants of the new *Geranium* have lighter green-colored leaves than plants of the male parent selection.
2. Plants of the new *Geranium* and the male parent selection differ in flower color as plants of the male parent selection have white-colored flowers.

Plants of the new Zonal *Geranium* can be compared to plants of the *Pelargonium×hortorum* cultivar 'KLEP01052', disclosed in U.S. Plant Pat. No. 13,202. In side-by-side comparisons conducted in Stuttgart, Germany, plants of the new Zonal *Geranium* differed from plants of the cultivar KLEP01052 in the following characteristics:

1. Plants of the new Zonal *Geranium* had larger leaves than plants of the cultivar KLEP01052.
2. Leaves of plants of the new Zonal *Geranium* were lighter green in color than leaves of plants of the cultivar KLEP01052.
3. Plants of the new Zonal *Geranium* and the cultivar KLEP01052 differed in flower color as plants of the cultivar KLEP01052 had white-colored flowers.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of typical flowering plants of 'KLEPZ05148' grown in a container.

DETAILED BOTANICAL DESCRIPTION

The photographs and following observations, measurements and values describe plants grown in Stuttgart, Germany in a glass-covered greenhouse during the summer and autumn and under conditions which closely approximate commercial *Geranium* production. During the production of the plants, day temperatures ranged from 18° C. to 22° C., night temperatures ranged from 14° C. to 18° C. and light levels ranged from 20,000 lux to 55,000 lux. Plants were about 2.5 months old when the photograph and the description were taken. In the detailed description, color references are made to The Royal Horticultural Society Colour Chart, 2001 Edition, except where general terms of ordinary dictionary significance are used.

Botanical classification: *Pelargonium×hortorum* cultivar KLEPZ05148.

Parentage:

*Female, or seed, parent.*—Proprietary selection of *Pelargonium×hortorum* identified as code number Z W 001, not patented. Male or pollen parent: Proprietary selection of *Pelargonium×hortorum* identified as code number Z BS 001, not patented.

Propagation:

*Type.*—By vegetative terminal cuttings.

*Time to initiate roots, summer.*—About ten days at temperatures of 22° C.

*Time to initiate roots, winter.*—About twelve days at temperatures of 20° C.

*Time to produce a rooted young plant, summer.*—About 18 days at temperatures of 22° C.

*Time to produce a rooted young plant, winter.*—About 20 days at temperatures of 20° C.

*Root description.*—Medium in thickness, fibrous; white in color.

*Rooting habit.*—Freely branching, moderately dense.

Plant description:

*Plant/growth habit.*—Upright to rounded plant habit; densely foliated. Moderately vigorous growth habit. Freely basal branching habit with about three to four lateral branches per plant.

*Plant height, to top of umbels.*—About 26 cm to 32 cm.

*Plant height, to top of leaves.*—About 18 cm to 22 cm.

*Plant width.*—About 27 cm to 29 cm.

*Lateral branches.*—Length: About 8 cm to 9 cm. Internode length: About 1.5 cm to 2 cm. Texture: Pubescent. Color: 146B.

Foliage description:

*Arrangement.*—Alternate; simple.

*Length.*—About 8 cm to 10 cm.

*Width.*—About 8 cm to 10 cm.

*Shape.*—Reniform.

*Apex.*—Rounded.

*Base.*—Cordate.

*Margin.*—Crenate.

*Venation pattern.*—Palmate.

*Texture, upper and lower surfaces.*—Slightly pubescent; rough.

*Color.*—Developing and fully expanded foliage, upper surface: 146A; venation, 146C. Developing and fully expanded foliage, lower surface: 146B; venation, 146C. Zonation pattern: Not observed. Petiole: Length: About 8 cm to 9 cm. Diameter: About 2.5 mm. Texture, upper and lower surfaces: Rough. Color, upper and lower surfaces: 146A.

Flower description:

*Flower arrangement.*—Semi-double rotate flowers arranged in rounded hemispherical umbels arising from apical leaf axils. Umbels displayed above the foliage on strong peduncles. Flowers face upright to outward; flowers slightly cupped. Flowers not persistent. Flowers not fragrant.

*Quantity of flowers.*—Freely flowering habit; about 30 to 40 flower buds and open flowers per umbel.

*Flowering season.*—Year-round under greenhouse conditions. In the garden in Stuttgart, Germany, flowering is continuous from spring until frost in autumn.

*Flower longevity.*—Individual flowers last about six to twelve days on the plant.

*Umbel height.*—About 5 cm to 6 cm.

*Umbel diameter.*—About 8 cm to 10 cm.

*Flower diameter.*—About 3.5 cm.

*Flower depth (height).*—About 1.5 cm.

*Flower buds.*—Length: About 1 cm. Diameter: About 5 mm to 6 mm. Shape: Elliptic. Color: 138A.

*Petals.*—Quantity per flower: About five or six. Length: About 2 cm. Width: About 1.5 cm. Shape: Ovate. Apex: Rounded. Base: Attenuate. Margin: Entire. Texture, upper and lower surfaces: Smooth, glabrous; velvety. Color: When opening, upper and lower surfaces: 4C. Fully opened, upper surface: 4D; towards the base, 4C; venation, 4C. Fully opened, lower surface: 4D; venation, 4D.

*Petaloids.*—Quantity per flower: None to about three. Length: About 2 mm to 6 mm. Width: About 1 mm. Shape: Irregularly shaped. Apex: Rounded. Base: Attenuate. Margin: Entire. Texture, upper and lower surfaces: Smooth, glabrous; velvety. Color: When opening, upper and lower surfaces: 4C. Fully opened, upper and lower surfaces: 4D; venation, 4D.

*Sepals.*—Quantity per flower: Five, arranged in a single whorl. Length: About 5 mm to 6 mm. Width: About 1 mm to 2 mm. Shape: Elliptic. Apex: Acute. Base: Obtuse. Margin: Entire. Texture, upper and lower surfaces: Rough. Color, upper and lower surfaces: 138A.

*Peduncle (umbel stem).*—Length: About 16 cm to 22 cm. Diameter: About 3 mm to 5 mm. Strength: Strong. Angle: Mostly erect. Texture: Slightly pubescent. Color: 138A.

*Pedicel* (*individual flower stem*).—Length: About 2 cm to 2.5 cm. Diameter: About 1.5 mm. Strength: Moderately strong. Angle: Erect to about 110° C. from vertical. Texture: Slightly pubescent. Color: 138A.

*Reproductive organs.*—Androecium: Stamen quantity per flower: About five. Anther length: About 2 mm to 3 mm. Anther shape: Ovate. Anther color: 29B. Pollen amount: Scarce. Pollen color: 28B. Gynoecium: Pistil quantity per flower: One. Pistil length: About 6 mm. Stigma shape: Tapering; reflexed. Stigma color: 4C. Style length: About 2 mm. Style color: 4C. Ovary color: 137D.

*Seed.*—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 12° C. to about 35° C. and have demonstrated good garden performance.

It is claimed:

1. A new and distinct Zonal *Geranium* plant named 'KLEPZ05148' as illustrated and described.

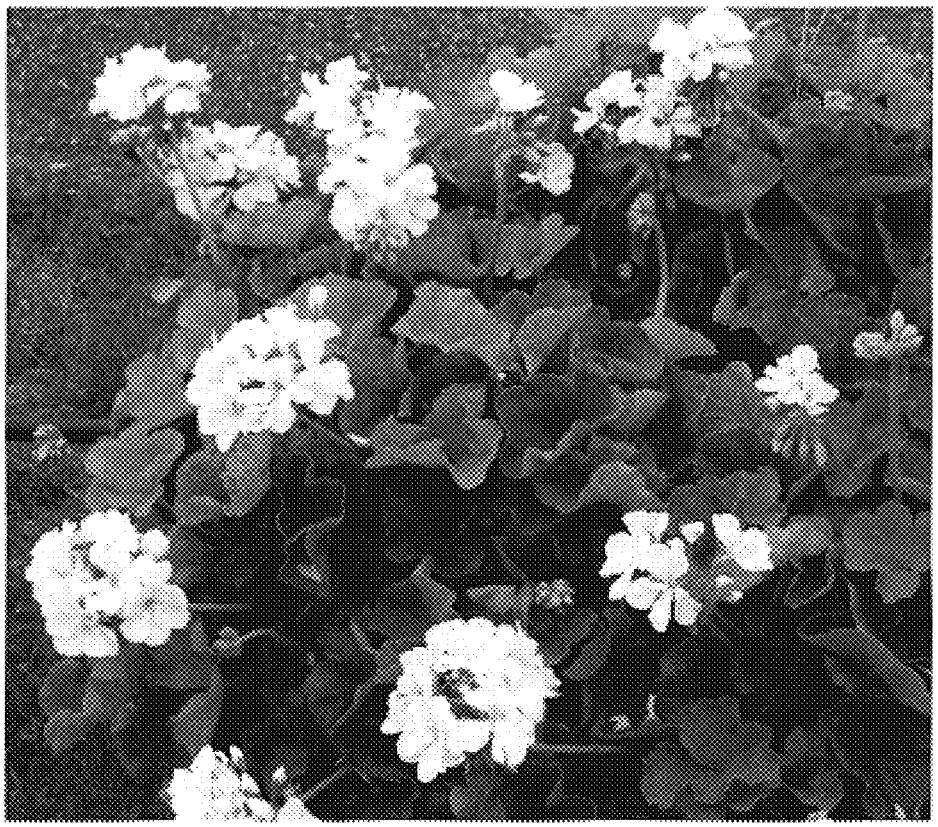

* * * * *